United States Patent [19]

Müller

[11] 4,115,460

[45] Sep. 19, 1978

[54] METHOD FOR PRODUCING HEXACHLOROCYCLOBUTENE

[75] Inventor: Wolfgang Müller, Marl, Fed. Rep. of Germany

[73] Assignee: Chemische Werke Huls AG, Marl, Fed. Rep. of Germany

[21] Appl. No.: 772,904

[22] Filed: Feb. 28, 1977

[30] Foreign Application Priority Data

Feb. 28, 1976 [DE] Fed. Rep. of Germany ...... 2618557

[51] Int. Cl.$^2$ ............................................ C07C 23/06
[52] U.S. Cl. .......................... 260/648 R; 203/DIG. 6; 203/99
[58] Field of Search ........ 260/648 R; 203/99, DIG. 6

[56] References Cited

U.S. PATENT DOCUMENTS

| | | | |
|---|---|---|---|
| 3,897,505 | 7/1975 | Walker et al. | 260/648 R |
| 3,963,446 | 6/1976 | Miller | 203/DIG. 6 |

Primary Examiner—C. Davis
Attorney, Agent, or Firm—Gilbert L. Wells

[57] ABSTRACT

Method for producing hexachlorocyclobutene from hexachlorobutadiene, wherein technical hexachlorobutadiene is rectified at a pressure of 2–10 mm Hg with a reflux ratio of 300–600, and the hexachlorobutadiene remaining in the sump during this procedure, after a heat treatment at 150°–200° C., is recycled into the rectifying column together with fresh, technical hexachlorobutadiene. The product rich in hexachlorocyclobutene, withdrawn overhead, is optionally subjected to a fractional crystallization.

5 Claims, 1 Drawing Figure

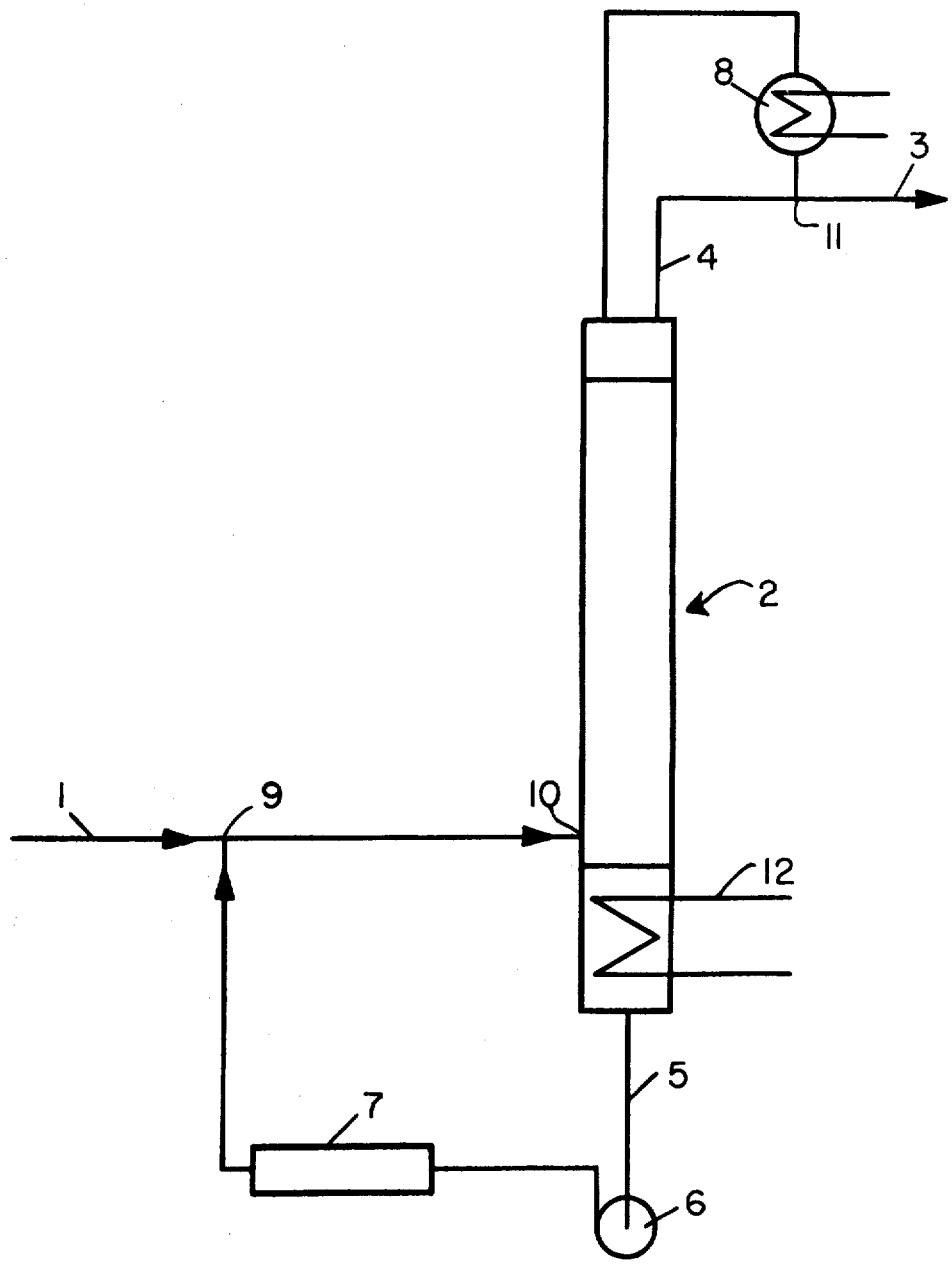

METHOD FOR PRODUCING HEXACHLOROCYCLOBUTENE

CROSS-REFERENCE TO A RELATED APPLICATION

Applicant claims priority for application P26 18 557.9 filed Apr. 28, 1976 in the Patent Office of the Federal Republic of Germany.

BACKGROUND OF THE INVENTION

The present invention relates to a process for the production of hexachlorocyclobutene from technical hexachlorobutadiene by cyclization of the hexachlorobutadiene to hexachlorocyclobutene and separation of the hexachlorocyclobutene by means of rectification.

Hexachlorobutadiene can be produced as a coproduct with carbon tetrachloride in the manufacture of perchloroethylene as disclosed in Kirk-Othmer, "Encyclopedia of Chemical Technology", Volume 5, (1964) under the section "Carbon Tetrachloride" particularly pages 132 and 133, the disclosure of which is incorporated herein.

The technical hexachlorobutadeiene preferably used as the raw material in the present invention has a hexachlorobutadiene concentration of about 98 to 100 percent by weight and hexachlorocyclobutene concentration of about 0 to 2 percent by weight. This technical hexachlorobutadiene is prepared as disclosed in U.S. Pat. No. 2 960 543 or Japanese Pat. No. 73 42615 (examinated application).

Hexachlorocyclobutene is an interesting intermediate product for the synthesis of organic compounds. This compound is obtained in the laboratory by reacting hexafluorocyclobutene with aluminum chloride. From technical hexachlorobutadiene, hexachlorocyclobutene can be enriched up to approximately 20% by vacuum fractionation and low-temperature crystallization ("Angew. Chemie"[Applied Chemistry] 78 [1966] p. 928, last paragraph, to page 929, third paragraph). It is furthermore known that hexafluoro-and hexachlorobutadiene can be arranged in an equilibrium reaction into hexafluoro-and hexachlorocyclobutene, respectively. In the case of the hexafluoro derivative, the cyclic structure is more stable from a thermodynamic viewpoint, while the openchain structure is greatly preferred in the case of hexachlorobutadiene ("Angew. Chemie") 78 [1966]p. 928, last paragraph, to p. 929, second paragraph). In accordance with this publication, a cyclization of the hexachlorobutadiene to hexachlorocyclobutene was to be just as unsuitable as a purification by means of distillation, since a 20% enrichment is completely insufficient from a commercial viewpoint.

SUMMARY OF THE INVENTION

Having in mind the limitations of the prior art, it is an object of the present invention to produce hexachlorocyclobutene of a high purity in an economical manner from raw materials which are commercially readily accessible.

This object is achieved according to the present invention by rectifying technical hexachlorobutadiene, which contains hexachlorocyclobutene, under reduced pressure at a high reflux ratio, and recycling the hexachlorobutadiene remaining in the sump, after a heat treatment, together with fresh, technical hexachlorobutadiene into the rectifying column, while the product rich in hexachlorocyclobutene withdrawn overhead is optionally subjected to a fractional crystallization.

BRIEF DESCRIPTION OF THE DRAWING

The drawing appended hereto is a schematic side view of the apparatus used in the present invention.

Raw material is introduced at 1, blended with recycled material at 9 and introduced into distillation column 2 at 10. The vapors are condensed in condenser 8 and separated at 11 with a first portion of the condensate withdrawn via conduit 3 and a second portion is refluxed into the column via conduit 4. The sump is maintained at temperature by heat exchanger 12.

A stream of substance is withdrawn from the sump by way of conduit 5 and recycled through furnace 7 to 9 by means of pump 6.

DESCRIPTION OF THE PREFERRED EMBODIMENTS

Hexachlorobutadiene containing hexachlorocyclobutene is formed as an undesired by-product in the manufacture of perchlorinated hydrocarbons. By means of a heat treatment at about 125°–200° C., preferably 180°–200° C. during a residence time of about 2–120 minutes, preferably 3–10 minutes, the hexachlorobutadiene is cyclized to hexachlorocyclobutene to an extent of about 1.0 –1.9%. By separating the thus-formed hexachlorocyclobutene by rectification and by conducting a repeated heat treatment of the hexachlorobutadiene, practically the entire amount of hexachlorobutadiene is rearranged into the hexachlorocyclobutene.

The rectification is conducted in a column having 50–150, preferably 70–100 theoretical plates. Suitable are columns with packings of wire mesh rings, wire meshes, as well as generally columns having a low pressure drop per theoretical separating stage.

The rectification is carried out under a pressure of about 2–100 mm Hg, preferably 15–50 mm Hg, at a sump temperature of about 100°–140° C., preferably 110°–120° C., and with a reflux ratio of about 300–600, preferably 350–500. During this procedure, the temperature in the enrichment section of the column, corresponding to the zone from the first to the 100th theoretical plate, preferably from the tenth to the 100th theoretical plate, is preferably maintained at below 120° C. When producing a high-percentage hexachlorocyclobutene, it is furthermore advantageous to keep, at a distillation pressure of 3–30 mm Hg, the temperature of the cooling medium in the condenser at above the melting point of hexachlorocylobutene, for example at 51° C.

Almost pure hexachlorocyclobutene is crystallized from mixtures of hexachlorocyclobutene and hexachlorobutadiene wherein the hexachlorocyclobutene is highly enriched. This crystallization occurs, from 80% strength hexachlorocyclobutene, already at about 44° C. Therefore, it is also possible to conduct the rectification only up to a concentration of, for example 80%, and to purify the hexachlorocyclobutene by a fractional crystallization.

Of special advantage is the continuous production of hexachlorocyclobutene, by rectifying in the aforementioned way a product freed of other substances, for example, by rectification and consisting primarily of hexachlorobutadiene besides small proportions of hexachlorocyclobutene. Thus the head product obtained is a high-percentage hexachlorocyclobutene, while continuously a partial stream is from the sump of the rectifying column and, after heating this partial stream to temperatures of, for example, 200° C., is recycled to the rectifying column. This recycling can take place into the sump or, even more advantageously, at the level of the feed point for the raw material. From such a device, it is possible to withdraw practically the entire introduced amount of hexachlorobutadiene with perhaps minor proportions of hexachlorocyclobutene in the form of a high-percentage hexachlorocyclobutene from the head of the column.

EXAMPLE

In an experimental arrangement, corresponding to the schematic illustration of the drawing, the crude hexachlorobutadiene, which has been subjected to a preliminary distillation to separate other components, as it is obtained, for example, in a plant for the manufacture of carbon tetrachloride and perchloroethylene by the chlorination of mixtures of various chlorinated hydrocarbons, such as chloroform, dichloroethane, and others, is introduced via pipeline 1 into the distillation column 2. The column employed is a column having a height of 10 m. packed with wire mesh (a so called "Sulzer" column) with about 70 theoretical plates. The feed point is approximately 1 meter above the column sump. The vapors are completely condensed in condenser 8, and a first portion of the condensate is withdrawn via conduit 3, whereas the reflux is recycled into the column via conduit 4. A stream of substance is withdrawn from the sump by way of conduit 5 and recycled to the rectifying column by means of the pump 6 by way of the furnace 7. The pressure at the head of the column is maintained at 25 mm. Hg, thus obtaining, with a reflux ration of 450, a temperature of 101° C at the head of the column. A product having 98.6% hexachlorocyclobutene, with the remainder being hexachlorobutadiene is thus withdrawn, having a melting point of approximately 50.0° C. A concentration of 1.1% by weight of hexachlorocyclobutene is determined in the column sump, whereas, downstream of the furnace 7, a concentration of 1.8% of hexachlorocyclobutene is measured. The feed likewise has this concentration. With a differential pressure of the column of 21 mm Hg, the sump temperature is 120° C. In the furnace 7, the product is heated to 200° C. with an average residence time of approximately 10 minutes.

I claim:

1. Method for producing hexachlorocyclobutene from hexachlorobutadiene, comprising;
    (a) rectifying in a rectification column technical hexachlorobutadiene at a pressure of about 2-100 mm Hg with a reflux ration of about 300-600, and removing a head product and a sump stream of substance;
    (b) heat treating said sump stream of substance at a temperature of about 150°-200° C to cyclize hexachorobutadiene to hexachlorocyclobutene enriched hexachlorobutadiene; and
    (c) recycling said enriched hexachorobutadiene into said rectifying together with fresh, technical hexachlorobutadiene.

2. The method of claim 1, wherein said head product is subjected to a fractional crystallization.

3. The method of claim 1, wherein said rectification column has 70-100 theoretical plates under a pressure of 15-50 mm Hg and with a reflux ratio of 350-500.

4. The method of claim 1, wherein said enriched hexachlorobutadiene has a hexachlorocyclobutene concentration of about 1.0 to 1.9 percent by weight.

5. The method of claim 1 wherein said rectification column has 100 theoretical plates and the 10th to the 100th of said theoretical plates define an enrichment section and said enrichment section is maintained at below 120° C.